(12) United States Patent
Wu et al.

(10) Patent No.: US 6,372,239 B1
(45) Date of Patent: Apr. 16, 2002

(54) COMPOSITIONS AND METHODS FOR CONTROLLING PESTS USING SYNERGISTIC COCKTAILS OF PLANT ALKALOIDS

(75) Inventors: Chang-An Wu; Hong Wu, both of Tian Jin; Ling Lei, Meishan, all of (CN)

(73) Assignee: GreenTech, Inc., Burlingame, CA (US)

( * ) Notice: Subject to any disclaimer, the term of this patent is extended or adjusted under 35 U.S.C. 154(b) by 0 days.

(21) Appl. No.: 09/655,613

(22) Filed: Sep. 6, 2000

(30) Foreign Application Priority Data

Jan. 28, 2000 (CN) .......................................... 00100591

(51) Int. Cl.$^7$ ........................ A01N 25/00; A01N 43/00; A01N 43/40; A61K 31/44
(52) U.S. Cl. ........................ 424/405; 504/130; 514/183; 514/343
(58) Field of Search ................................ 504/146, 138, 504/130; 514/183, 343; 424/405

(56) References Cited

FOREIGN PATENT DOCUMENTS

| EP | 0 796 621 A3 | 3/1997 | .......... A61K/35/78 |
| EP | 0 796 621 A2 | 3/1997 | .......... A61K/35/78 |

OTHER PUBLICATIONS

Zhou et al, Anti–inflammatory and antiallergic action of aloperine, Zhongguo Taoli Xuebao, 10(4), 360–5, 1989.*

Sapronov et al, Pharmacology of anabasis aphylla alkaloids anabasine and anabasamine, Farmakol. Toksikol. (Moscow) 1982, 45(6), 25–7, 1982.*

Wanchun et al, The toxicities of alkaloids from sophora alopecuroids against turnip aphids and effect on several esterases, 1997, XP–000995481, pp. 365–372.*

L. Wanchun et al., "Toxicity of Cytisine Against the Mustard Aphid Lipaphis Erysimi Kaltenbach (Homoptera: Aphididae) and its Effect on Esterases", 1999, *Pesticide Biochemistry and Physiology*, vol. 65, No. 1, pp. 1–5.

L. Wanchun et al., "The Toxicities of Alkaloids from Sophora Alopecuroids Against Turnip Aphids and Effect on Several Esterases", *Acta Entomologica Sinica*, Nov. 1997, vol. 40, pp. 358–365.

* cited by examiner

*Primary Examiner*—Alton Pryor
(74) *Attorney, Agent, or Firm*—Wilson Sonsini Goodrich & Rosati

(57) ABSTRACT

Compositions and methods are provided for killing and controlling pests by using cocktails of plant alkaloids. In one embodiment, the pesticidal composition comprises: anabasine; and one or more plant alkaloids selected from the group consisting of toosendanin, azadirachtin, tomatine, nicotine, matrine, oxymatrine, sophocarpine, N-oxysophocarpine, cytisine, and aloperine. The pesticide can be used to protect crop plants, wood structures and animals from damages by harmful pests, overcome resistance of pests to current commercial pesticides, and reduce contamination to the environment.

28 Claims, 5 Drawing Sheets

Acetylcholine

Nicotine

Anabasine

Toosendanin

Azadirachtin

Matrine

Oxymatrine

Sophocarpine

N-Oxysophocarpine

Cytisine

Aloperine

Ricinine

Harmaline (3,4-Dihydroharmine)

|  | $R_1$ | $R_2$ |
|---|---|---|
| Triptonide | H | =O |
| Tripdiolide | OH | OH |
| Triptolide | H | OH |

Euphol

COMPOSITIONS AND METHODS FOR CONTROLLING PESTS USING SYNERGISTIC COCKTAILS OF PLANT ALKALOIDS

BACKGROUND OF THE INVENTION

1. Field of the Invention

This invention relates to compositions and methods for controlling pest, and, more particularly, to pesticides that are derived from natural substances, such as plant alkaloids.

2. Description of Related Art

Infestation of pests continues to threaten the health of humans and animals, and causes damages to plants, wood structures and households. In particular, some 10,000 species of the more than 1 million species of insects are crop-eating, and of these, approximately 700 species worldwide cause most of the insect damage to man's crops, in the field and in storage.

Our ancestors have used a wide variety of natural materials to protect plants from insects since 1000 B.C. For example, the earliest records of insecticides pertain to the burning of "brimstone" (sulfur) as a fumigant. Even gall from green lizard was used to protect apples from worms and rot. Later, whitewash, lye, brine, vinegar, extracts of pepper and tobacco, and fish oil were used to control pests and repel biting and tickling insects.

Since the World War II (1940), attention has been focused on synthetic pesticidal chemicals that can be synthesized economically and used in large amounts to control insects on plants and in households. Thomson WT (1998) Agriculture Chemicals, Book I, "Insecticides", Thomson Publications, Fresno, Calif. These synthetic organic insecticides can be classified into many types of chemicals, including organochlorines, organophosphates, organosulfurs, carbamates, formamidines, dinitrophenols, organotins, pyrethroids, nicotinoids, spinosyns, fiproles, pyrroles, pyrazoles, pyridazinones, quinazolines, and benzoylureas.

The organochlorines are insecticides that contain carbon, hydrogen, and chlorine. The oldest group of the organochlorines is the diphenyl aliphatics, which included DDT, DDD, dicofol, ethylan, chlorobenzilate, and methoxychlor. More than 4 billion pounds of DDT were used throughout the world, beginning in 1940, and ending essentially in 1973, when the U.S. Environmental Protection Agency canceled all uses. Other organochlorines include hexchlorocyclohexane (HCH), cyclodienes, and polychloroterpens.

The organophosphates (OPs) are the most widely used synthetic pesticidal chemicals. Other names that are known for this type of pesticide are organic phosphates, phosphorus insecticides, nerve gas relatives, and phosphoric acid esters. All organophosphates are derived from one of the phosphorus acids, and as a class are generally the most toxic of all pesticides to vertebrates. Because of the similarity of OP chemical structures to the "nerve gases", their modes of action are also similar. Their insecticidal qualities were observed in Germany during World War II in the study of the extremely toxic OP nerve gases sarin, soman, and tabun.

The OPs have two distinctive features: they are generally much more toxic to vertebrates than other classes of insecticides, and most are chemically unstable or nonpersistent. It is this latter characteristic that brought them into agricultural use as substitutes for the persistent organochorines.

The OPs work by tying up or inhibiting certain important enzymes of the nervous system, namely cholinesterase (ChE). The enzyme is shown to be phosphorylated when it becomes attached to to the phosphorous moiety of the insecticide, a binding that is irreversible. This inhibition results in the accumulation of acetylcholine (ACh) at the neuron/neuron and neuron/muscle (neuromuscular) junctions or synapses, causing rapid twitching of voluntary muscles and finally paralysis.

The OPs, originally developed as nerve gases during the World War II, can impose serious dangers to people exposed to this type of chemicals. The OPs attack the brain and nervous system, even short-term exposure can cause damage. Symptoms include headaches, nausea, dizziness, seizures, and in extreme cases can result in paralysis, coma, and death.

Safer pesticides have been derived from plants such as tobacco, pyrethrum, derris, hellebore, quassia, and camphor. In particular, pyrethroids, synthetic or extracted from chrysanthemum, are widely used as insecticides in many countries.

Unfortunately, long-term use of a single type of pesticides that have similar mechanisms of action can result in pesticide resistance and resurgence of pests. Resistance and resurgence of pests represents a major problem in agriculture. To date, more than 500 species, including rats, mice, German cockroaches, mosquitos, Drosphilia melanogaster, and tobacco bud worms, are known to have developed resistance to the toxic effects of a variety of pesticides. Pesticide resistance is characterized by multiple mechanisms including increased detoxification, reduced absorption of applied pesticides, increased tolerance of the pesticide by the targeted pest, and increased elimination by the pest of the applied pesticide. Such resistance interjects elements of uncertainty when applying pesticides to target pest and can require a regimen of increasing application rates or ever-changing pesticides to overcome or prevent the development of resistance. Increasing the amount, frequency or rate of pesticide application, in turn, can generate a more serious problem of accumulating residual pesticide on plants and environmental contamination as to soil, air, and water.

SUMMARY OF THE INVENTION

The present invention provides novel compositions and methods for controlling pests, in particular, for killing insects that cause harmful effects to plants, wood, and animals. The compositions of the present invention may be used as a pesticide to prevent and protect plants from damages caused by insects, to prevent and reduce damages caused by termite to wood structures, and to protect and cure animals infested with harmful insects and microorganisms.

The compositions of the present invention comprise cocktails of plant alkaloids that are combined to exert its insecticidal activity via multiple pathways of signal transduction. The alkaloids in the compositions possess a variety of structures and functions which may contribute to the synergistic lethal effects of the compositions on a broad spectrum of insects.

In one embodiment, the composition of the present invention comprises: anabasine; and one or more plant alkaloids selected from the group consisting of toosendanin, azadirachtin, tomatine, nicotine, matrine, oxymatrine, sophocarpine, N-oxysophocarpine, cytisine, and aloperine. Optionally, the composition comprises two, three, four or more members of this group.

According to the embodiment, the alkaloid anabasine may be chemically synthesized. Alternatively, anabasine may be extracted from plants such as Anabasis aphylla, Nicotiana acuminata, Duboisia myoporoides, Zinnia elegans, and Zollikoferia eliquiensis. When extracted, anabasine may be in a pure form, a semi-purified form, or may be a component of an unpurified plant extract.

Also according to the embodiment, the one or more plant alkaloids may be chemically synthesized. Alternatively, the one or more plant alkaloid may be extracted from plants. When extracted, they may be in a pure form, a semi-purified form, or may be a component of an unpurified plant extract.

For example, toosendanin may be extracted from the plants Melia toosendan Sieb. et Zucc. and Melia azedarach L. Azadirachtin may be extracted from the plant Melia azedarach L. Tomatine may be extracted from Lycopersicon esculentum. The alkaloids, matrine, oxymatrine, sophocarpine, and N-oxysophocarpine, may be extracted from the plants Sophora flavescens Ait., and Sophora alopecuroides L. Cytisine and aloperine may be extracted from Sophora alopecuroides L.

In a variation of the embodiment, the composition further comprises a plant alkaloid selected from the group consisting of ricinine, harmaline, stellerin, euphol, triptonide, tripdiolide, and triptolide.

According to the variation, the plant alkaloids may be synthesized chemically, or extracted from plants. For example, ricinine may extracted from Ricinus communis L. Harmaline may be extracted from Peganum harmala L. Stellerin and euphol may be extracted from Stellera chamaeiasme L. The alkaloids, triptonide, tripdiolide, and triptolide, may be extracted from Tripterygium Wilfordii Hook F.

In one particular variation, the composition comprises: anabasine, toosendanin, and one or more alkaloids contained in the plant Sophora alopecuroides L. such as matrine, oxymatrine, sophocarpine, N-oxysophocarpine, cytisine, and aloperine.

In another particular variation, the composition comprises: anabasine, nicotine and toosendanin.

In another embodiment, the composition of the present invention comprises: harmaline; and one or more plant alkaloids selected from the group consisting of toosendanin, azadirachtin, tomatine, nicotine, anabasine, matrine, oxymatrine, sophocarpine, N-oxysophocarpine, cytisine, and aloperine. Optionally, the composition comprises two, three, four or more members of this group.

In yet another embodiment, the composition the pesticide of the present invention comprises: toosendanin, stellerin and one or more alkaloids contained in the plant Sophora alopecuroides L. such as matrine, oxymatrine, sophocarpine, N-oxysophocarpine, cytisine, and aloperine.

In yet another embodiment, the composition of the present invention comprises: toosendanin, harmaline and one or more alkaloids contained in the plant Sophora alopecuroides L. such as matrine, oxymatrine, sophocarpine, N-oxysophocarpine, cytisine, and aloperine.

In any of the above embodiments, the composition may further comprise an alkaloid selected from the group consisting of syemonine, aconitine, rotenone, and arteannuine.

These alkaloids may be synthesized chemically or extracted from plants. For example, syemonine may be extracted from Radix stemonae. Aconitine may be extracted from the plants Aconitum kusnezoffii reichb and Common monkshood mother root. Rotenone may be extracted from the plant Derris trifoliate lour. Arteannuine may be extracted from the plant Herba artemisiae annuae.

In any of the above embodiment, the composition may further comprise a solvent. Any solvent may be used to dissolve or disperse the composition, preferably a solvent that is generally regarded as safe (GRAS) for agriculture and household uses. Examples of solvents that may be used include, but are not limited to, pentane, hexane, heptane, octane, nonane, decane, isooctane, cyclohexane, petroleum distillates, petroleum ether, benzene, toluene, chlorobenzene, benzaldehyde, xylene, butanol, pentanol, hexanol, kerosene, diesel, turpentine and mixtures thereof.

In a preferred embodiment, the solvent for the composition is turpentine.

In any of the above embodiments, the pesticide may further comprise an emulsifier or a surfactant. Any emulsifier may be used to enhance the solubility and/or stabilize the composition, preferably an emulsifier that is generally regarded as safe (GRAS) for agriculture and household uses.

Optionally, the composition may further comprise a combination of emulsifers with complementary hydrophilic and hydrophobic parameters. For example, the emulsifiers may be a combination of nonionic surfactant and anionic surfactant.

Examples of nonionic surfactant include, but are not limited to, polyoxyethylated alkylphenols (e.g., octylphenol and nonylphenol), polyoxyethylated sorbitan monoesters, polyoxyethylated fatty or aryl-alkyl alcohols, fatty acids and esters (e.g. TWEEN® 40–80).

Examples of anionic emulsifier include, but are not limited to, alkyl, alkyl-aryl and aryl sulfonates, sulfates and phosphates, soaps (i.e., salts of carboxylic acids with at least 8 carbon atoms).

Optionally, the compositions may comprise an acidifying agent, an alkaline agent, an antioxidant, or any other agent which may be used to enhance the chemical stability of the alkaloids included in the composition.

In any of the above embodiments, the composition may comprise one or more solid agents for creating a dry, solid pesticide, or for timed release of the composition, such as powder, dust, microspheres, or pellets. These formulations may be used to stabilize the alkaloids prior to dilution with a solvent or may serve to allow the application of the composition to plants as a solid.

The concentration of each alkaloid in the composition before dilution and application may preferably be between about 0.1%–10% (w/v), more preferably between about 0.2%–2% (w/v), and most preferably between about 0.4%–1% (w/v).

The stability of the composition before dilution and application may preferably be between 80–100%, more preferably 90–100%, and most preferably 95–100% retained pesticidal activity after two years of storage at room temperature.

The compositions of the present invention can be used to protect plants, wood, and animals from harmful effects of insects. The composition may be diluted with water or other solvent and sprayed to crop plants indoor, inside a greenhouse, in a garden, and in the field. The composition may also be fumigated to kill insects in a closed environment or in the field. In addition, the composition may also be used to bath livestock and pets to kill insects that infested these animals. The composition may also be used to dust plants and fields.

DETAILED DESCRIPTION OF THE INVENTION

Figure 1:
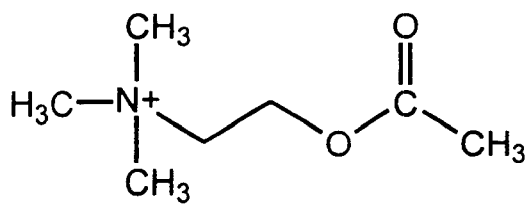
FIG. 1 shows the chemical structures of acetylcholine, nicotine, and anabasine.
Figure 1:
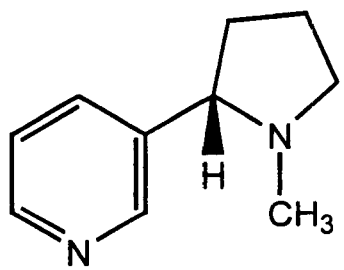
Figure 1:
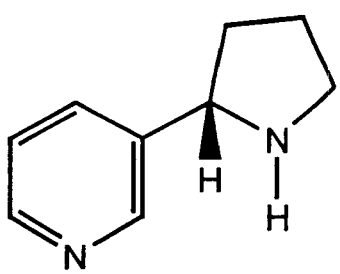

The present invention provides novel compositions and methods for controlling pests and preventing or reducing damage resulted from pest infestation. The compositions of the present invention can be used as pesticides that are effective, economical and environmentally friendly.

The compositions of the present invention are pesticides that are combinations of botanicals with plant alkaloids as the active ingredients. The plant alkaloids, such as anabasine, toosendanin, and aloperine, can be chemically synthesized or extracted from plants such as Anabasis aphylla L., Melia azedarach L., and Sophora alopecuroides L., respectively. These alkaloids can be dissolved or emulsified in various solvents in the present or absent of an emulsifier.

Formed as a cocktail of active ingredients, the composition of the present invention should be a more effective pesticide than that having a single active ingredient such as an organochlorine (e.g., hexchlorocyclohexane) and an organophosphate (e.g., melathion). Due to the different chemical structures and funstions of the plant alkaloids, a pesticide with a cocktail of these ingredients has lethal effects on the pests by multiple mechanisms of actions. For example, pests can be killed by both the contact and stomach activities of these alkaloids.

Pests should be less capable of developing resistance to the compositions of the present invention due to the multiple pathways of action that the active ingredients possess. By targeting multiple lethal pathways of the pests simultaneously, the composition not only kills the pests effectively but also reduces reproductivity and the ability of the surviving pests to develop mutations that enhances their tolerance to the various active ingredients. Eggs of the pests can also be killed by the composition, thus further reducing the chance of resurgence of the pests.

The compositions of the present invention should have less "residue" problems as compared to pesticides made of synthetic organic insecticides widely used in the world. The alkaloids are natural ingredients derived from plants and, when applied to plants infected by pests, can be easily degraded by microorganisms in the soil (biodegradation), or decomposed by exposing to water (hydrolysis) and to air (oxidation). In contrast, many synthetic organic insecticides are resistant to biodegradation and decomposition due to exposure to other environmental elements such as rain and air. As a result, these organic chemicals remain on the plant long after the application of the pesticides and pose a great threat to the health of people who eat the vegetables or fruits from these plants. Since the plant alkaloids in the composition of the present invention are mostly composed of these four essential elements: carbon, hydrogen, oxygen and nitrogen, they can be easily degraded into carbon dioxide and water by microorganisms in the soil. They not only protect the plant by killing the pests infested on but also provide nutrients to the soil after the degradation of the natural ingredients in the pesticide.

1. The Plant Alkaloids

The compositions of the present invention comprise a combination of plant alkaloids that are formulated to control pests. The alkaloids as active ingredients may control the pests by mulitple mechanisms and signal transduction pathways. Although killing of adult or immature insects may be desirable, pest control may also be equivalently accomplished in ways other than those that result in death. For example, an increased level of avoidance by insects of a plant or animal may constitute an effective level of control, i.e. having an anti-feeding effect. Thus, even if mortality is not high, beneficial control can be realized.

In the present invention, "pest control" is intended to encompass all forms of control including but not limited to insecticide, larvicide, nymphicide, and ovicide activities as well as anti-feeding activities. In non-insect targets, control can be attained at any stage of the life cycle. Particular combinations of alkaloids according to the present invention may be particularly effective on one or another stage of the life cycle of the pests.

In the course of further discussing the invention, the inventors do not wish to be bound by a particular mechanism or explanation of action, as such understanding is not necessary for the practice of the invention. Within this context, however, the inventors hypothesize the mechanisms of action of a few plant alkaloids of the present invention in causing death and regulating the life cycle of pests.

a) Anabasine

Anabasine, 2-(3-pyridyl)-3,4,5,6,-tetrahydropyridine, belongs to the family of tobacco alkaloid. Anabasine can be chemically synthesized by following Smith (1935) J. Am. Chem. Soc. 57:959. Anabasine can also be extracted from Anabsis aphylla L. Anabasine is a potent activator of vertebrate neuromuscular nicotinic acetylcholine receptors. Both nicotine and anabasine prossess a non-aromatic ring attached to the 3-position of a pyridyl ring (FIG. 1). Anabasine's non-aromatic tetrahydropyridine ring imine double bond is conjugated with p-electrons of the 3-pyridyl ring. The imine nitrogen is a much weaker base than the pyrrolidinyl nitrogen of nicotine.

Anabasine mimics the action of acetylcholine (FIG. 1), which is a major excitatory neurotransmitter in the insect central nerve system (CNS). After acetylcholine is released by the presynaptic cell, it binds to the postsynaptic nicotinic acetylcholine receptor and activates an intrinsic cation channel. This results in a depolarization of the postsynaptic cell due to an influx of sodium and calcium ions. The synaptic action of acetylcholine is terminated by the enzyme acetylcholinesterase, which rapidly hydrolyzes the ester linkage in acetylcholine. Anabasine also activates the nicotinic acetylcholine receptor, and does so persistently, since it is insensitive to the action of acetylcholinesterase. This persistent activation leads to an overstimulation of cholinergic synapses, and results in hyperexcitation, convulsion, paralysis, and death of the insect.

b) Toosendanin

Figure 2:
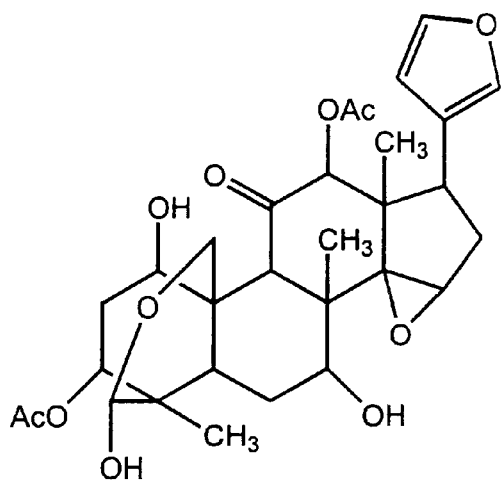
FIG. 2 shows the chemical structures of toosendanin and azadirachtin.

The chemical structure of toosendanin is shown in FIG. 2. Toosendanin has a molecular weight of 574.60, is colorless crystal, dissolves in methanol, chloroform and petroleum ether, and has a melting. point of 244–245° C.

As shown in FIG. 2, due to some structural similarity, toosendanin may mimic the function of azadirachtin in the control of pests. Like azadirachtin, toosendanin may act as an antifeedant, a metamorphosis disrupter, a chemosterilant and a weak toxicant.

In one aspect, toosendanin may exert its antifeeding effects by preventing insects from feeding. Toosendanin is non-volatile, so an insect must taste it, rather than smell it, in order to respond to it. A taste of toosendanin stimulates at least one 'deterrent neurone' in insects which show an antifeedant response. The strength of 'deterrent neurone' responses has been correlated with the strength of antifeedant responses.

In another aspect toosendanin may also be able to regulate growth of insects by disrupting the molting process of insects. Toosendanin may disrupt molting by inhibiting biosynthesis or metabolism of ecdysone, the juvenile molting hormone.

A requisite for developmental growth in insects is molting. Molting is the entire process by which an insect's old cuticle is shed. The process of molting is initiated when the insect molting hormone ecdysterone (20-hydroxyecdysone) stimulates the epidermis to retract from the cuticle. This retraction of the epidermis from the cuticle is termed "apolysis". Apolysis is immediately followed by mitotic division of the epidermal cells and their subsequent secretion of a protective procuticle and a gel-like molting fluid. Following activation of the molting fluid, enzymatic digestion of the old cuticle for resorption and reuse results in a thin (i.e., undigested) remnant of the old cuticle which is subsequently split and cast off by the insect. This remnant of the old cuticle which is eventually split and cast off is called the "exuvia". The casting off of the exuvia is termed "ecdysis". Ecdysis is accomplished by hydrostatic pressure brought about by the swallowing of air or water by the insect and its subsequent performance of muscular activities.

When a new cuticle is synthesized, it is soft and flexible so that the hydrostatic pressures brought about by the insect unfold and expand it. In this way, the new cuticle increases its surface area and the old cuticle is concomitantly cast off.

After ecdysis, expansion of the new cuticle is brought to an end by the onset of "sclerotization". Sclerotization involves the cross-linking of cuticular protein with ortho-quinone. The source of the ortho-quinone is tyrosine, whose mobilization is controlled by ecdysterone and a peptide hormone called bursicon.

Thus by inhibiting biosynthesis or metabolism of ecdysone, the normal process of molting is disrupted which results in production of deformed insects, leading to decreased reproductivity and increased mortality.

c) Alkaloids from Sophora alopecuroides L.

Figure 3:
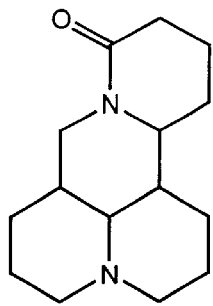
FIG. 3 shows the chemical structures of matrine, oxymatrine, sophocarpine, N-oxysophocarpine, cytisine and aloperine.
Figure 3:
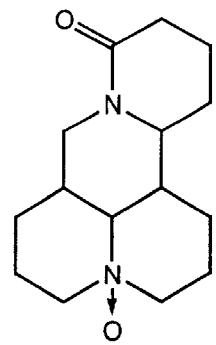
Figure 3:
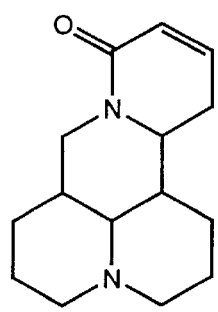
Figure 3:
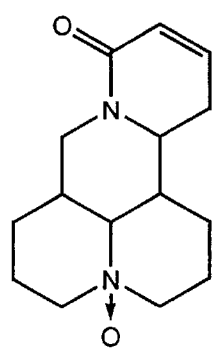
Figure 3:
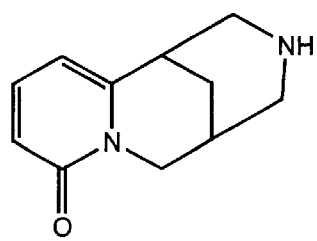
Figure 3:
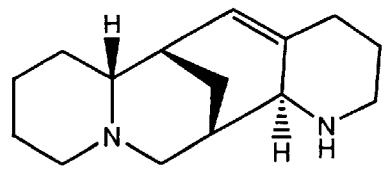

The plant Sophora alopecuroides L. contains many different alkaloids including matrine, oxymatrine, sophocarpine, N-oxysophocarpine, cytisine and aloperine. The chemical structures of these alkaloids are shown in FIG. 3.

The insectidal activity of these alkaloids may be attributed to their inhibitory effects on acetylcholinesterase. By inhibiting this enzyme, the degradation of the neurotransmitter acetylcholine is blocked. The synaptic concentrations of acetylcholine then builds up and hyperexcitation of the CNS occurs, which eventually results in the death of pests.

2. The Combinations of Plant Alkaloids

The present invention provides novel combinations of plant alkaloids that can be used for controlling pests, in particular, for killing insects that cause harmful effects to plants, wood, and animals. The compositions of the present invention may be used to as pesticide to prevent and protect plants from damages caused by insects, to prevent and reduce damages caused by termites to wood structures, and to protect and cure animals infested with harmful insects and microorganisms.

As discussed above, the compositions of the present invention comprise cocktails of plant alkaloids that are combined to exert its insecticidal activity via multiple pathways of signal transduction. The alkaloids in the compositions possess a variety of structures and functions which may contribute to the synergistic lethal effects of the compositions on a broad spectrum of insects.

In one embodiment, the composition of the present invention comprises: anabasine; and one or more plant alkaloids selected from the group consisting of toosendanin, azadirachtin, tomatine, nicotine, matrine, oxymatrine, sophocarpine, N-oxysophocarpine, cytisine, and aloperine. The composition may comprise two, three, four or more of the above plant alkaloids.

According to the embodiment, the alkaloid anabasine may be chemically synthesized. Alternatively, anabasine may be extracted from plants such as Anabasis aphylla, Nicotiana acuminata, Duboisia myoporoides, Zinnia elegans, and Zollikoferia eliquiensis. When extracted, anabasine may be in a pure form, a semi-purified form, or may be a component of an unpurified plant extract.

Also according to the embodiment, the one or more plant alkaloids may be chemically synthesized. Alternatively, the one or more plant alkaloid may be extracted from plants. When extracted, they may be in a pure form, a semi-purified form, or may be a component of an unpurified plant extract.

Figure 4:
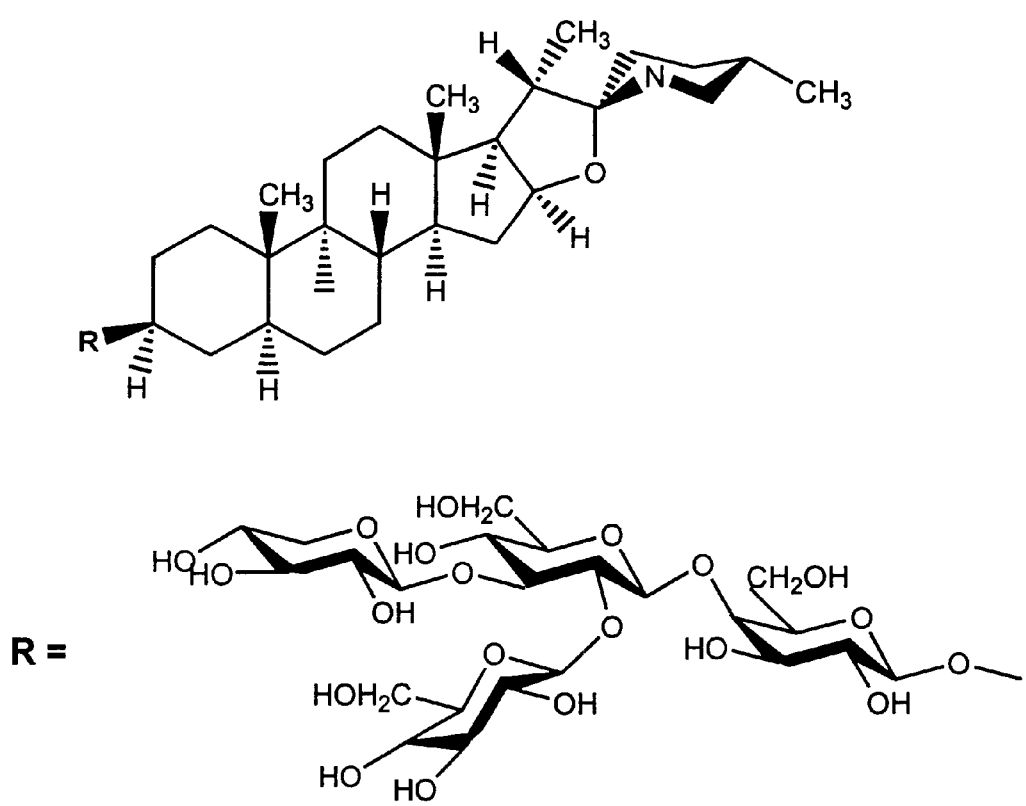
FIG. 4 shows the chemical structure of tomatine.

For example, toosendanin may be extracted from the plant Melia toosendan Sieb. et Zucc. Tomatine (chemical structure shown in FIG. 4) may be extracted from Lycopersicon esculentum. The alkaloids, matrine, oxymatrine, sophocarpine, and N-oxysophocarpine, may be extracted from the plants Sophora flavescens Ait., and Sophora alopecuroides L. Cytisine and aloperine may be extracted from Sophora alopecuroides L.

In a variation of the embodiment, the composition further comprises a plant alkaloid selected from the group consisting of ricinine, harmaline, stellerin, euphol, triptonide, tripdiolide, and triptolide.

Figure 5:
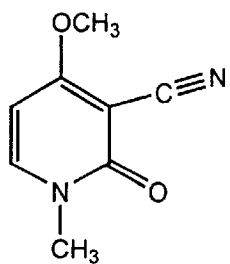
FIG. 5 shows the chemical structures of ricinine, harmaline, triptonide, tripdiolide, triptolide, and euphenol.
Figure 5:
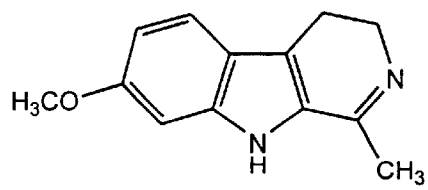
Figure 5:
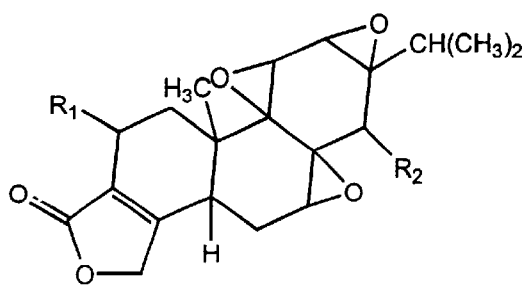
Figure 5:
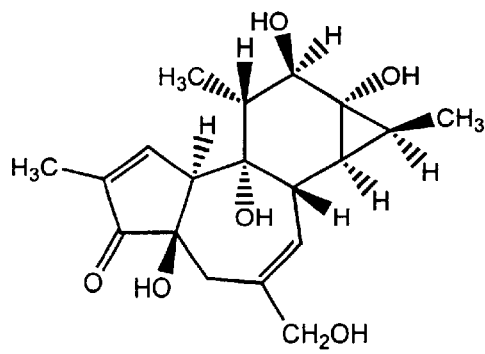

According to the variation, the plant alkaloids may be synthesized chemically, or extracted from plants. For example, ricinine (chemical structure shown in FIG. 5) may extracted from Ricinus communis L. Harmaline (chemical structure shown in FIG. 5) may be extracted from Peganum harmala L. Stellerin and euphol (chemical structure shown in FIG. 5) may be extracted from Stellera chamaelasme L. The alkaloids, triptonide, tripdiolide, and triptolide (chemical structures shown in FIG. 5), may be extracted from Tripterygium Wilfordii Hook F.

In one particular variation, the composition comprises: anabasine, toosendanin, and one or more alkaloids contained in the plant Sophora alopecuroides L. such as matrine, oxymatrine, sophocarpine, N-oxysophocarpine, cytisine, and aloperine.

In another particular variation, the composition comprises, the pesticide comprises: anabasine, nicotine and toosendanin.

In another embodiment, the pesticide of the present invention comprises: harmaline; and one or more plant alkaloids selected from the group consisting of toosendanin, azadirachtin, tomatine, nicotine, anabasine, matrine, oxymatrine, sophocarpine, N-oxysophocarpine, cytisine, aloperine, and combinations thereof. The composition may comprise two, three, four or more of the above plant alkaloids.

In yet another embodiment, the composition of the present invention comprises: toosendanin; and one or more alkaloids contained in the plant Sophora alopecuroides L. such as matrine, oxymatrine, sophocarpine, N-oxysophocarpine, cytisine, and aloperine.

In yet another embodiment, the composition of the present invention comprises: toosendanin, stellerin and one or more alkaloids contained in the plant Sophora alopecuroides L. such as matrine, oxymatrine, sophocarpine, N-oxysophocarpine, cytisine, and aloperine.

In yet another embodiment, the composition of the present invention comprises: toosendanin, harmaline and one or more alkaloids contained in the plant Sophora alopecuroides L. such as matrine, oxymatrine, sophocarpine, N-oxysophocarpine, cytisine, and aloperine.

In any of the above embodiments, the pesticide may further comprise an alkaloid selected from the group consisting of syemonine, aconitine, rotenone, and arteannuine.

These alkaloids may be synthesized chemically or extracted from plants. For example, syemonine may be extracted from Radix stemonae. Aconitine may be extracted from the plants Aconitum kusnezoffli reichb and Common monkshood mother root. Rotenone may be extracted from the plant Derris trifoliate lour. Arteannuine may be extracted from the plant Herba artemisiae annuae.

3. Preparation of the Plant Alkaloids

Plant alkaloids contained in the composition of the present invention may be chemically synthesized at industrial scales in large amounts. Alternatively, the alkaloids may be extracted from natural raw materials from plants. The level of extraction and the degree of purity of alkaloid may vary. For example, unpurified plant extracts may be employed in the present invention. Depending on the solubility of the particular plant alkaloid in water or in organic solvent, the extraction process for each alkaloid may differs. Alternatively, the alkaloid may be partially purified or completely purified. Chemical synthesis of the alkaloid obviates the need for extraction and purification.

The present invention provides two methods for extracting the alkaloids from raw plant materials: organic solvent extraction, and aqueous-organic solvent extraction.

a) Organic solvent extraction

The organic extraction method of the present invention involves a step of continuous washing and extracting the plant material against a stream of organic solvent. Examples of organic solvents include, but are not limited to methanol, ethanol, dichloromethane, chloroform, xylene, and petroleum ether.

For example, such an organic solvent extraction can be conducted in an extracting machine. Raw materials collected from the plant which contains the desired alkaloid(s), such as leaves, barks, seeds, and/or roots, are first ground to small particle sizes, and then put into the extracting machine through an inlet for the raw materials by a measurable charging machine. The plant materials are pushed by a thruster in the extracting machine and move forward slowly. Organic solvent (e.g. ethanol) is added into the machine through a solvent inlet at the top of a waste discharging outlet. Due to the difference of gravity and equilibrium, the solvent flows toward the raw material inlet, soaks the materials and flows out from the opposite side of the solvent inlet. Since the plant materials and the solvent move in opposite directions against each other, the plant materials are constantly immersed in a solution that contains low-concentration of extracted alkaloid(s). As a result of equilibrium, high yield of plant alkaloid(s) can be achieved by continuously extracting the plant material against the low-concentration solution.

The time of extraction may be preferably between about 1–8 h, more preferably between about 2–6 hr, and most preferably between about 3–5 hr.

The temperature of extraction may be preferably between about 30–90° C., more preferably between about 40–70° C., and most preferably between about 50–60° C.

The collected extract is then fine-filtered to remove debris, and concentrated by distilling the solvent until the solid content reaches between about 25% and 45%. The distilled solvent can be reused for extraction.

b) Aqueous-organic solvent extraction

Raw materials collected from a plant which contains the desired alkaloid(s), such as leaves, barks, seeds, and/or roots, are first ground to small particle sizes. The grounded plant material is soaked in aqueous solution that is acidic or alkaline, depending on the solubility and stability of the desire alkaloid(s) under acidic or alkaline (basic) condition. For extraction under acidic condition, acid such as hydrochloric acid, sulfuric acid can be added into water at concentration of about 3% (w/v). For extraction under alkaline condition, alkali such as sodium hydroxide and sodium carbonate can be added into water.

The time of extraction is preferably between about 1–8 h, more preferably between about 2–6 hr, and most preferably between about 3–5 hr.

The temperature of extraction is preferably between about 30–90 °C, more preferably between about 40–70° C, and most preferably between about 50–60° C.

The extract is then collected and fine-filtered to remove debris. Alkaline (e.g. ammonia) or acidifying agents (e.g. sulfuric acid) may be added to the extract to neutralize the solution by adjusting the pH, depending on the acidity or alkalinity of the collected extract. Organic solvent is then added to the neutralized solution to extract the alkaloid from aqueous phase to organic phase. Examples of such organic solvent include, but are not limited to, butanol, pentanol, hexanol and xylene. The extracted alkaloid(s) dissolved in organic solvent is concentrated until the solid content reaches about 50–80%.

It should be noted that different plants containing different kinds of alkaloids may be mixed and extracted together. This process of mixed extraction may preferably be used for extracting those plants containing alkaloids with similar solubility in the solvent used for extraction. For example, the plants, Sophora alopecuroides L. (containing aloperine, matrine, etc.), Melia toosendan sieb. et Zucc. (containing toosendanin), and Stellera chamaeiasme L. (containing stellerin), may be mixed, grounded, and extracted in ethanol. The mixture of alkaloids extracted can be concentrated and stored in appropriate solvent (e.g. turpentine) and emulsifier.

4. Formulation of the Compositions of the Present Invention

The concentrated alkaloid(s) extracted from each plant can be mixed and diluted by using the same solvent for storing the concentrated alkaloid(s), or by using a different solvent that can solubilize most if not all of the alkaloids in the mixture.

Any solvent may be used to dissolve or disperse the alkaloids, preferably a solvent that is generally regarded as safe (GRAS) for agriculture and household uses. Examples of solvents include, but are not limited to, pentane, hexane, heptane, octane, nonane, decane, isooctane, cyclohexane, petroleum distillates, petroleum ether, benzene, toluene, chlorobenzene, benzaldehyde, xylene, butanol, pentanol, hexanol, kerosene, diesel and turpentine.

In a preferred embodiment, the solvent for the composition is turpentine. One of the advantages of using turpentine as solvent for the composition is that turpentine is a natural oil from pine trees and is generally regarded as safe for household uses.

The composition may further comprise an emulsifier. Any emulsifier may be used to enhance the solubility and/or stabilize the composition, preferably an emulsifier that is generally regarded as safe (GRAS) for agriculture and household uses. A wide variety of emulsifiers can be used in the formulation of the composition of the present invention. The emulsifier may be a nonionic or an ionic surface-active agent (surfactant).

Examples of nonionic surfactant include, but are not limited to, polyoxyethylated alkylphenols, polyoxyethylated alkylphenols (e.g., octylphenol and nonylphenol), polyoxyethylated sorbitan monoesters, polyoxyethylated fatty or aryl-alkyl alcohols, fatty acids and esters (e.g. TWEEN® 40–80).

Examples of anionic emulsifier include, but are not limited to, alkyl, alkyl-aryl and aryl sulfonates, sulfates and phosphates, soaps (i.e., salts of carboxylic acids with at least 8 carbon atoms).

Examples of cationic emulsifiers include, but are not limited to, quaternary ammonium salts and salts of primary, secondary and tertiary amines containing at least one hydrocarbon moiety with 8 or more carbon atoms, and ampholytic emulsifiers in their zwitterionic or monojonic forms.

For single nonionic emulsifier, the HLB (hydrophile-lipophile balance) number is preferably between 6–18, more preferably between 7–16, and most preferably 8–14.

Optionally, the composition may further comprise a combination of emulsifers with complementary hydrophilic and hydrophobic parameters. For example, the emulsifiers may be a combination of a nonionic surfactant and an anionic surfactant. Pairs of nonionic emulsifiers, one with a high HLB (e.g. HLB 17–18) number that is water soluble and almost oil insoluble, the other with a low HLB (e.g. HLB 5–6) that is almost water insoluble but soluble in the oil phase, the combined HLB of the such pairs of emulsifiers is preferably between 6–18, more preferably between 7–16, and most preferably 8–14.

The concentration of the total alkaloids in the formulation is preferably between about 0.1–20% (w/v), more preferably about 1–10% (w/v), and most preferably 2–5% (w/v).

The concentration of the emulsifier(s) in the formulation is preferably between about 0.1–10% (w/v), more preferably about 1–5% (w/v), and most preferably 2–4% (w/v).

The amount of organic solvent(s) in the formulation is preferably between about 10–80% (w/v), more preferably about 20–60% (w/v), and most preferably 30–40% (w/v).

The amount of water in the formulation is preferably between about 10–80% (w/v), more preferably about 20–60% (w/v), and most preferably 30–40% (w/v).

Optionally, the compositions of the present invention may comprise an acidifying agent, an alkaline agent, an antioxidant, or any other agent which may be used to enhance the chemical stability of the alkaloids included in the compositions.

Also optionally, the composition may comprise one or more solid agents for creating a dry, solid pesticide, or for timed release of the composition, such as powder, dust, microspheres, or pellets. These formulations may be used to stabilize the alkaloids prior to dilution with a solvent or may serve to allow the application of the composition to plants as a solid.

The composition of the present invention can be used to protect plants, wood, and animals from harmful effects of insects. The composition may be diluted with water and sprayed onto crop plants indoor, inside a greenhouse, in a garden, and in the field. The composition may also be injected into the bark of a tree to prevent and protect it from pest infestation. Moreover, the pesticide may be fumigated to kill insects in a closed environment or in the field. In addition, the pesticide may also be used to bath livestock and pets to kill insects that infested these animals.

EXAMPLES

1. Extraction of alkaloids from slants

The plant alkaloids of the present invention can be extracted from natural raw materials by using the methods of organic solvent extraction or aqueous-organic solvent extraction described above. The following are examples showing how to extract the alkaloids from particular plants in details.

1) Extraction of alkaloids from Sophora alopecuroides

Dried Sophora alopecuroides (with roots removed) was ground and added into an extracting machine. By using the method of organic solvent extraction, the raw material was extracted against methanol at a weight ratio of 1:6 (plant:methanol). After fine-filtration and concentration, the extract was transferred into turpentine and stored in a cool, dark place. The alkaloids extracted from Sophora alopecuroides include matrine, oxymatrine, sophocarpine, N-oxysophocarpine, cytisine and aloperine. The content of total alkaloids was 30%.

2) Extraction of toosendanin from Melia toosendan Sieb. et Zucc.

Dried seeds from Melia toosendan Sieb. et Zucc. were ground and extracted against methanol by using a similar method used for extracting alkaloids from Sophora alopecuroides. After fine-filtration and concentration, the extract containing toosendanin was transferred into turpentine and stored in a cool, dark place. The content of toosendanin was 20%.

3) Extraction of anabasine from Anabasis aphylla

Anabasine was extracted from Anabasis aphylla by using the aqueous-organic method described above. Dried plant from Anabasis aphylla was ground into powder. The powder was added into an alkaline aqueous solution containing sodium hydroxide at 2%. The mixture was heated at 90–95° C. for 3 hours. After being cooled and filtrated, the extract was treated with diluted sulfuric acid to adjust pH to 6.0–6.5. Anabasine in the neutralized extract was then extracted against butanol, which results in the transfer of anabasine from the aqueous phase to the organic phase. Extract from the organic phase was collected and concentrated until the content of anabasine reached about 30%. This concentrated stock solution of anabasine was stored in a cool, dark place.

4) Extraction of alkaloids from a mixture of plants

The alkaloids, aloperine, toosendanin, and stellerin, were extracted together from a mixture of plants, Sophora alopecuroides, Melia toosendan Sieb. et Zucc., and Stella chamaeiasme L. Sophora alopecuroides (50 Kg), and Melia toosendan Sieb. et Zucc. (20 Kg), and roots of Stella chamaeiasme L. (30 Kg) were ground and mixed. This mixture of plant raw material was added into an extraction container into which 500 Kg of 95% ethanol was added. The ratio of solid to liquid is about 1:5. The mixture was heated to 60° C. and stirred for 3 hours. The ethanol solution was filtered and collected as the first extract. The remaining mixture of plant materials was extracted again in 300 Kg of 95% ethanol by heating it at 60° C. for 3 hours. The second extract was filtered and combined with the first extract. The combined extract was concentrated by distilling ethanol from the solution under vacuum condition until the weight of the extract dropped to about 30 Kg and solid content reached about 30%.

2. Formulation of the compositions of the present invention

The extracts of alkaloids from individual plants may be combined to form a cocktail pesticidal composition. For example, in one embodiment, extracts that contain Sophora alopecuroide alkaloids (in turpentine, 1.5 Kg), toosendanin (in turpentine, 1.5 Kg) and anabasine (in butanol, 1.0 Kg)

which were isolated from individual plants were mixed. Warm turpentine (44 Kg) which had been heated at 60° C. was added to this mixture of alkaloids. Eight kilograms of emulsifier (e.g. Twin 80) was then added to the mixture which was stirred for 15 min. The remaining warm turpentine (44 Kg) was added into the mixture. When cooled to about 30° C., this cocktail of alkaloids was bottled and will be referred to herein as "GT-fresh".

Alternatively, the alkaloids that were extracted from a mixture of plants can be formulated directly based on the concentrated stock mixture. For example, concentrated stock (30 Kg) containing a mixture of the alkaloids, aloperine, toosendanin, and stellerin, which were extracted together from a mixture of plants as described above was mixed 8 Kg of emulsifier. This mixture was heated to 60–70° C. and stirred quickly. Turpentine (32.7 Kg) was added into the heated mixture which was then emulsified for 10 min. More turpentine (30 Kg) was added into the mixture and stirred for 5 min. When cooled to about room temperature, this cocktail of alkaloids was bottled as a pesticidal composition according to the present invention.

3. Tests of the pesticidal activity of the alkaloid cocktails

1) Insecticidal activity on pests infesting tea trees

A pesticide (GT) containing Sophora alopecuroide alkaloids, toosendanin and anabasine in turpentine that was prepared freshly from raw plant materials (GT-fresh) was diluted 1000 folds with water and applied to tea trees infested with small green leafhopper, snout beetle, red mite, and tea caterpillar. The times lapsed before the death of these insects and percentage of insects killed are shown in Table I.

TABLE I

Insecticidal activity of GT-fresh.

| INSECT NAME | DILUTION | DEATH TIME (hr) | EFFICIENCY (%) |
|---|---|---|---|
| Small green leafhopper | 1000x | 2.5 | 100 |
| Snout beetle | 1000x | 4.0 | 100 |
| Red beetle | 1000x | 2.0 | 100 |
| Tea caterpiilar | 1000x | 1.5 | 100 |

As shown in Table I, GT-fresh has strong pesticidal effects on the common pests to tea treas, small green leafhopper, snout beetle, red mite, and tea caterpillar. All of these pests died within 2–4 hr of application of the pesticide. Thus, by using GT-fresh, tea trees can be protected from the harm effects of these pests.

To evaluate the stability of the pesticidal compositions according to the present invention, pesticidal activity was tested for GT (a cocktail of Sophora alopecuroide alkaloids, toosendanin and anabasine in turpentine) that has been stored on shelf for 22 months, referred herein as "GT-stored". Table II shows the test results.

TABLE II

Insecticidal activity of GT-stored.

| INSECT NAME | DILUTION | DEATH TIME (hr) | EFFICIENCY (%) |
|---|---|---|---|
| Small green leafhopper | 1000x | 3.5 | 100 |
| Snout beetle | 1000x | 4.0 | 100 |
| Red beetle | 1000x | 3.0 | 100 |
| Tea caterpillar | 1000x | 2.5 | 100 |

As shown in Table II, GT-stored was still as effective as GT-fresh, a composition freshly prepared from plant extract, despite two years of storage. This demonstrates that the pesticidal compositions prepared and formulated according to the methods of the present invention have a shelf-stability of at least 2 years.

The inseticidal activity of a composition according to the present invention that was freshly extracted from raw plant materials (GT-fresh) was also compared with that of a commercial pesticide, pyrethrin chlorocyanide. Both pesticides were diluted 1000 folds with water and sprayed to tea trees infested with green leafhoppers in the field. Table III shows the test results.

TABLE III

Comprison of insecticidal activity of GT-fresh with a commercial pesticide (pyrethrin chlorocyanide, PC).

| Pesticide Name | Pest Counts Before Spray | First day Pests | First day Efficiency (%) | Third day Pests | Third day Efficiency (%) |
|---|---|---|---|---|---|
| PC | 74 | 58 | 9.4 | 52 | 9.7 |
| GT-fresh | 74 | 20 | 68.7 | 8 | 84.6 |

As shown in Table III, GT-fresh has much higher pesticidal activity than that of pyrethrin chlorocyanide (PC). It is known that small green leafhopper has developed resistance to pyrethrin chlorocyanide. The results shown in Table III confirmed that pyrethrin chlorocyanide is much less effective in killing these pests than GT-fresh.

The inseticidal activity of GT-stored was also compared with that of pyrethrin chlorocyanide. Both pesticidal compositions were diluted 1000 folds with water and sprayed to tea trees infested with green leafhoppers in the field. Table IV shows the test results.

TABLE IV

Comprison of insecticidal activity of GT-stored with pyrethrin chlorocyanide (PC).

| Pesticide Name | Pest Counts Before Spray | First day Pests | First day Efficiency (%) | Third day Pests | Third day Efficiency (%) | Fifth day Pests | Fifth day Efficiency (%) |
|---|---|---|---|---|---|---|---|
| PC | 40 | 43 | −7 | 40 | 0 | 40 | 0 |
| GT-stored | 44 | 14 | 68.2 | 8 | 77.1 | 8 | 77.1 |

As shown in Table IV, GT-stored, was still as effective as the one prepared freshly from raw plant materials (GT-fresh). In contrast, pyrethrin chlorocyanide (PC) was essentially ineffective in killing small green leafhopper on the treated tea tree.

2) Insecticidal activity on red mite infesting orange trees

GT-fresh was diluted 500 fold with water and applied to orange trees infested with red mite in the field. The insecticidal efficiency of GT-fresh was compared with that of water in Table V.

TABLE V

Insecticidal activity of GT-fresh on red mites

| Pesticide Name | Pest counts Before Spray | 24 hr after spray | | 48 hr after spray | | 72 hr after spray | |
|---|---|---|---|---|---|---|---|
| | | Pests | Efficiency (%) | Pests | Efficiency (%) | Pests | Efficiency (%) |
| GT-fresh | 71 | 21 | 70.4 | 19 | 73.2 | 13 | 81.7 |
| water | 68 | 67 | 1.5 | 67 | 1.5 | 66 | 3.0 |

As shown in Table V, GT-fresh was highly effective in killing red mite on orange trees in the field.

3) Insecticidal activity on aphid infesting sear trees

GT-fresh was diluted 500 fold with water and applied to pear trees infested with aphids in the field. The insecticidal efficiency of this pesticide was compared with that of water in Table VI.

TABLE VI

Insecticidal activity of GT-fresh on aphids

| Pesticide Name | Pest Counts Before Spray | 24 hr after spray | | 48 hr after spray | |
|---|---|---|---|---|---|
| | | Pests | Efficiency (%) | Pests | Efficiency (%) |
| GT-fresh | 590 | 390 | 33.9 | 98 | 83.4 |
| water | 654 | 650 | 0.6 | 648 | 1.2 |

As shown in Table VI, GT-fresh was highly effective in killing aphids on pear trees in the field.

4) Insecticidal activity on cabbage worms infesting cabbage

GT-fresh was diluted 500 fold with water and applied to 20 heads of cabbage infested with cabbage worms in the field. The insecticidal efficiency of this pesticide was compared with that of water in Table VII.

TABLE VII

Insecticidal activity of GT-fresh on cabbage worms

| Pesticide Name | Pest Counts Before Spray | 24 hr after spray | | 48 hr after spray | | 72 hr after spray | |
|---|---|---|---|---|---|---|---|
| | | Pests | Efficiency (%) | Pests | Efficiency (%) | Pests | Efficiency (%) |
| GT-fresh | 46.6/head | 4 | 91.5 | 1 | 97.7 | 0 | 100 |
| Water | 50.4/head | 26.2 | 48.1 | 16.8 | 66.6 | 15 | 70.2 |

As shown in Table VII, GT-fresh was highly effective in killing cabbage worms on cabbage in the field. It was noted that contact activity of this pesticide was particularly high. Once sprayed with the pesticide, the cabbage worms died almost immediately (within minutes).

What is claimed is:

1. A composition consisting essentially of:
   anabasine;
   toosendanin; and
   one or more plant alkaloids selected from the group consisting of tomatine, nicotine, matrine, oxymatrine, sophocarpine, N-oxysophocarpine, cytisine, aloperine, ricinine, harmaline, stellerin, euphol, triptonide, tripdiolide, and triptolide,
   wherein the composition is formulated to function as a pesticide.

2. The composition of claim 1, wherein anabasine is at concentration of between about 0.1%–10%.

3. The composition of claim 1, wherein anabasine is at concentration of between about 0.2%–2%.

4. The composition of claim 1, wherein anabasine is at concentration of between about 0.4%–1%.

5. The composition of claim 1, wherein the composition is in solid state.

6. The composition of claim 1, wherein the composition is an emulsion.

7. The composition of claim 1, wherein the composition is a liquid suspension.

8. A composition consisting essentially of:
   an extract derived from a plant selected from the group consisting of Anobasis aphyila, Alicotiano acutninata, Duboisia myoporvides, Zinnia elegans, and Zomlikofeda eliquiensis, which contains anabasine;
   alopedne; and
   one or more plant alkaloids selected from the group consisting of toosendanin, tomatine, nicotine, matrine, oxymatrine, sophocarpine, N-oxysophocarpine, ricinine, harmaline, stellerin, euphol, triptonide, tripdiolide, and triptolide.

9. A composition consisting essentially of:
   anabasine;
   aloperine;
   one or more plant alkaloids selected from the group consisting of toosendanin, tomatine, nicotine, matrine, oxymatrine, sophocarpine, N-oxysophocarpine, ricinine, harmaline, stellerin, euphol, triptonide, tripdiolide, and triptolide; and
   a solvent selected from xylene, butanol, pentanol, hexanol, kerosene, diesel and turpentine,
   wherein the composition is formulated to function as a pesticide.

10. The composition of claim 9, wherein the solvent is turpentine.

11. A composition consisting essentially of:
    anabasine;
    aloperine;
    one or more plant alkaloids selected from the group consisting of toosendanin, tomatine, nicotine, matrine, oxymatrine, sophocarpine, N-oxysophocarpine, ricinine, harmaline, stellerin, euphol, triptonide, tripdiolide, and triptolide; and a surfactant selected from the group consisting of polyoxyethylated alkylphenols, polyoxyethylated sorbitan monoesters, polyoxyethylated aryl-alkyl alcohols, polyoxyethylated fatty acids, and polyoxyethylated aryl-alkyl esters, wherein the composition is formulated to function as a pesticide.

12. A pest control method comprising:

applying to an object an effective amount of a pesticidal composition, the active ingredients of the composition comprising anabasine, aloperine, and an alkaloid selected from the group consisting of toosendanin, azadirachtin, tomatine, nicotine, matrine, oxymatrine, sophocarpine, N-oxysophocarpine, harmaline, nicinine, stellerin, euphol, tripotonide, tripdiolide, and triptolide, wherein applying the pesticidal composition protects the object from pests, and the object is selected from the group consisting of a plant, an animal, and wood.

13. The method of claim 12 wherein anabasine is extracted from a plant.

14. The method of claim 13 wherein anabasine is extracted from the plant selected from the group consisting of Anabasis aphylla, Nicotiana acuminata, Duboisia myoporoides, Zinnia elegans, and Zollikoferia eliquiensis.

15. The method of claim 12, wherein toosendanin is extracted from Melia toosendon Sieb. et Zucc or Melia azederach L.

16. The method of claim 12, wherein tomatine is extracted from Lycopersicon esculentum.

17. The method of claim 12, wherein matrine, oxymatrine, sophocarpine, and N-oxysophocarpine are extracted from the plant consisting of Sophora flavescens Ait., rand Sophora alopecuroides L.

18. The method of claim 12, wherein aloperine is extracted from Sophaora alopecuroides L.

19. The method of claim 12, wherein ricinine is extracted from Ricinus communis L.

20. The method of claim 12, wherein harmaline is extracted from Peganum harmala L.

21. The method of claim 12, wherein stellerin and euphol are extracted from Stelera chamaeiasme L.

22. The method of claim 12, wherein triptonide, tripdiolide, and triptolide are extracted from Tripterygium wilfordii hook F.

23. The method of claim 12, wherein applying the pesticidal composition to the object includes spraying the composition to the object.

24. The method of claim 12, wherein applying the pesticidal composition to the object includes injecting the composition into the object.

25. The method of claim 12, wherein applying the pesticidal composition to the object includes fumigating the composition and contacting the object with the fumigant.

26. The method of claim 12, wherein applying the pesticidal composition to the object includes dusting the composition onto the object.

27. The method of claim 12, wherein the object is selected from the group consisting of livestock, pet animals, and humans.

28. A pest control method comprising:

applying to an object an effective amount of a pesticidal composition, the active ingredients of the composition consisting essentially of anabasine, toosendanin, and one or more alkaloid selected from the group consisting of azadirachtin, tomatine, nicotine, matrine, oxymatrine, sophocarpine, N-oxysophocarpine, harmaline, aloperine, cytisine, ricinine, stellerin, euphol, tripotonide, tripdiolide, and triptolide, wherein applying the pesticidal composition protects the object from pests, and the object is selected from the group consisting of a plant, an animal, and wood.

* * * * *

UNITED STATES PATENT AND TRADEMARK OFFICE
CERTIFICATE OF CORRECTION

PATENT NO. : 6,372,239 B1
DATED : April 16, 2002
INVENTOR(S) : Wu et al.

It is certified that error appears in the above-identified patent and that said Letters Patent is hereby corrected as shown below:

<u>Title page,</u>
Item [75], should read Inventors: Chang-An Wu, Hong Wu, both of Tian Jin, Lin Lei, Meishan, all of (CN)

Signed and Sealed this

Ninth Day of July, 2002

*Attest:*

*Attesting Officer*

JAMES E. ROGAN
*Director of the United States Patent and Trademark Office*